US006635663B1

(12) United States Patent
Zen

(10) Patent No.: US 6,635,663 B1
(45) Date of Patent: *Oct. 21, 2003

(54) PESTICIDAL EMULSIFIABLE CONCENTRATE

(75) Inventor: Shigekazu Zen, Osaka-fu (JP)

(73) Assignee: Sumitomo Chemical Company, Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/961,272

(22) Filed: Oct. 30, 1997

(30) Foreign Application Priority Data

Nov. 1, 1996 (JP) .............................. 8-291980

(51) Int. Cl.$^7$ .................. A01N 43/40; A01N 37/34; A01N 53/06; A01N 25/02
(52) U.S. Cl. .................. 514/345; 514/520; 514/521; 514/523; 514/531; 514/532; 514/543; 514/721; 514/785; 514/937
(58) Field of Search .................. 514/65, 345, 937, 514/531, 532, 520, 521, 523, 543, 721, 785

(56) References Cited

U.S. PATENT DOCUMENTS

| | | | | |
|---|---|---|---|---|
| 4,617,318 A | * | 10/1986 | Marei | 514/520 |
| 4,680,054 A | * | 7/1987 | Takematsu et al. | 504/232 |
| 4,751,225 A | * | 6/1988 | Nishida et al. | 514/277 |
| 5,190,745 A | | 3/1993 | Dohara et al. | 424/45 |
| 5,435,992 A | * | 7/1995 | Audegond et al. | 514/419 |
| 5,846,997 A | * | 12/1998 | Sirinyan et al. | 514/490 |
| 5,942,525 A | * | 8/1999 | Pennington et al. | 514/345 |

FOREIGN PATENT DOCUMENTS

| | | |
|---|---|---|
| EP | 0648414 A2 | 4/1995 |
| EP | 0740901 A2 | 11/1996 |
| GB | 507902 | 6/1939 |
| GB | 205017 | 1/1981 |
| WO | WO95/31898 | 11/1995 |
| WO | WO96/01047 | 1/1996 |

OTHER PUBLICATIONS

Marsden, Solvents Guide, Interscience Publishers, New York, 1963, pp. 372–373.*

* cited by examiner

*Primary Examiner*—John Pak
(74) *Attorney, Agent, or Firm*—Sughrue Mion, PLLC

(57) ABSTRACT

The present invention provides a low-irritant pesticidal emulsifiable concentrate comprising (a) 1 to 60% by weight of at least one pesticidal active ingredient compound selected from the group consisting of pyriproxyfen and a pyrethroid compound, (b) 2 to 15% by weight of at least one surfactant and (c) 15 to 90% by weight of at least one aromatic ester solvent represented by the formula:

Ar—X—COOR  [1]

or the formula:

RCOO—X—Ar  [2]

[wherein R represents non-aromatic group having 1 to 6 carbon atoms; Ar represents an aromatic group; and X represents a single bond or an alkylene group having 1 to 6 carbon atoms]. The pesticidal emulsifiable concentrate of the present invention can be used as an emulsion which is superior in emulsion stability when using after diluting with water, and has low irritation.

13 Claims, No Drawings

PESTICIDAL EMULSIFIABLE CONCENTRATE

The present invention relates to a low-irritant pesticidal emulsifiable concentrate which can be used as an emulsion which is superior in emulsion stability when using after diluting with water.

A pesticidal active ingredient compound is normally used in various forms which are easy to use, and one of a normal preparation for pyriproxyfen and a pyrethroid compound is an emulsifiable concentrate.

The pesticidal emulsifiable concentrate is normally composed of a pesticidal active ingredient compound, a surfactant and an organic solvent, and is used after diluting with water. Various trials are made in selection of surfactants, selection of organic solvents and their combinations on making the pesticidal emulsifiable concentrate in order to enhance the emulsion stability of emulsion obtained by diluting with water and to reduce toxicity, phytotoxicity to crops, etc. depending on the kind of the pesticidal active ingredient compound,.

An object of the present invention is to provide a pesticidal emulsifiable concentrate which is superior in emulsion stability on dilution with water and low irritant.

The present invention provides a pesticidal emulsifiable concentrate comprising (a) 1 to 60% by weight of at least one pesticidal active ingredient compound selected from the group consisting of pyriproxyfen and a pyrethroid compound, (b) 2 to 15% by weight of at least one surfactant and (c) 15 to 90% by weight of at least one aromatic ester solvent represented by the formula:

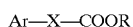

Ar—X—COOR     [1]

or the formula:

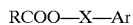

RCOO—X—Ar     [2]

[wherein R represents non-aromatic group having 1 to 6 carbon atoms; Ar represents an aromatic group; and X represents a single bond or an alkylene group having 1 to 6 carbon atoms] which is superior in emulsion stability on dilution with water and low irritant.

In the pesticidal active ingredient compound used in the present invention, examples of the pyrethroid compound includes compounds represented by the formula:

[3]

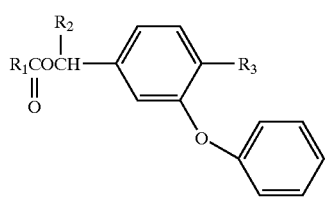

[Wherein $R_1$ represents a group of the formula:

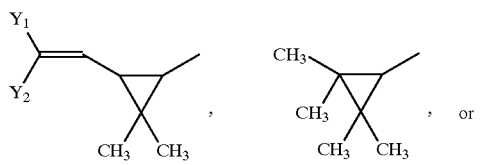
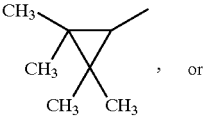

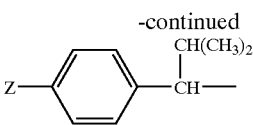

[wherein $Y_1$ and $Y_2$ are the same or different and each represents a methyl group, a trifluoromethyl group, a halogen atom or an alkoxycarbonyl group (the number of carbon atoms of the alkoxy group is from 1 to 4); and Z represents a halogen atom or a difluoromethoxy group]; $R_2$ represents a hydrogen atom or a cyano group; and $R_3$ represents a hydrogen atom or a fluorine atom].

Examples of the compounds represented by the formula [3] include pyrethroid compounds such as Fenvalerate [α-cyano-3-phenoxybenzyl 2-(4-chlorophenyl)-3-methylbutyrate], es-Fenvalerate [(S)-α-cyano-3-phenoxybenzyl (S)-2-(4-chlorophenyl)-3-methylbutyrate], Fenpropathrin [α-cyano-3-phenoxybenzyl 2,2,3,3-tetramethylcyclopropanecarboxylate], Permethrin [3-phenoxybenzyl 3-(2,2-dichlorovinyl)-2,2-dimethylcyclopropanecarboxylate], Cypermethrin [α-cyano-3-phenoxybenzyl 3-(2,2-dichlorovinyl)-2,2-dimethylcyclopropanecarboxylate], d-phenothrin [3-phenoxybenzyl (1R)-chrysanthemate], Cyphenothrin [α-cyano-3-phenoxybenzyl (1R)-chrysanthemate], Cyhalothrin [α-cyano-3-phenoxybenzyl (Z)-(2-chloro-3,3,3-trifluoropropenyl)-2,2-dimethylcyclopropanecarboxylate], Cyfluthrin [α-cyano-4-fluoro-3-phenoxybenzyl 3-(2,2-dichlorovinyl)-2,2-dimethylcyclopropanecarboxylate], Flucythrinate [α-cyano-3-phenoxybenzyl (S)-2-(4-difluoromethoxyphenyl)-3-methylbutyrate], etc.

It is also possible used pyrethroid compounds such as Tralomethrin [(S)-α-cyano-3-phenoxybenzyl 2,2-dimethyl-3-(1,2,2,2-tetrabromoethyl)cyclopropanecarboxylate], Allethrin [3-allyl-2-methyl-4-oxo-2-cyclopentenyl-chrysanthemate], Cycloprothrin [α-cyano-3-phenoxybenzyl 2,2-dichloro-1-(4-ethoxyphenyl)cyclopropanecarboxylate], Fluvalinate [α-cyano-3-phenoxybenzyl N-(2-chloro-α, α, α-trifluoro-p-tolyl)valinate], Etofenprox [2-(4-ethoxyphenyl)-2-methylpropyl 3-phenoxybenzyl ether], etc. as the pesticidal active ingredient compound in the pesticidal emulsifiable concentrate of the present invention.

The pesticidal active ingredient compound is contained in the pesticidal emulsifiable concentrate of the present invention in an amount of 1 to 60% by weight, preferably 2 to 40% by weight.

Examples of the surfactant used in the present invention include nonionic surfactants such as polyoxyethylene polyoxypropylene block polymer, fatty acid ester of polyoxyethylene polyoxypropylene block polymer, polyoxyethylene polyoxypropylene polyaryl ether, polyoxyethylene polyoxypropylene alkyl aryl ether, polyoxyethylene alkyl aryl ether, polyoxyethylene vegetable oil (e.g. polyoxyethylene castor oil), polyoxyethylene polyaryl ether, polyoxyethylene polyaryl ether polymer, polyoxyethylene hardened vegetable oil (e.g. polyoxyethylene hardened castor oil), polyoxyethylene fatty acid ester, polyoxyethylene alkyl ether, polyoxyethylene tristyryl phenylphosphate diester, polyoxyethylene polyoxypropylenetristyryl phenylphosphate diester, fatty acid alcohol polyglycol ether, glycerin fatty acid ester, etc.; and anionic surfactants such as alkaline earth metal salt (e.g. calcium salt) and amine salt of alkyl aryl phosphate, alkali earth metal salt (e.g. calcium salt) and amine salt of alkylaryl sulfonate, alkaline earth metal salt of polyoxyethylene alkyl aryl sulfonate, alkaline earth metal salt (e.g. calcium salt) of polyoxyethylene alkyl aryl phosphate, alkaline earth metal salt (e.g. calcium salt) of polyoxyethylene polyaryl phosphate, alkaline earth metal salt (e.g. calcium salt) and amine salt of dialkylsulfosuccinate, etc. Among them, polyoxyethylene polyaryl ether (e.g. polyoxyethylene tristyryl phenol ether), polyoxyethylene polyoxypropylene polyaryl ether (e.g. polyoxyethylene polyoxypropylene tristyrylphenol ether), polyoxyethylene castor oil, polyoxyethylene hardened castor oil, and salt of alkyl aryl sulfonate (e.g. calcium dodecylbenzene sulfonate) are preferred. The surfactant is contained in the pesticidal emulsifiable concentrate of the present invention in an amount of 2 to 15% by weight, preferably 2 to 10% by weight.

In the aromatic ester solvent used in the present invention, Ar of formula [1] and formula [2] is preferably a phenyl group which may be substituted with at least one methyl group, etc.; X is preferably a single bond, a methylene group or an ethylene group; R is preferably an alkyl group having 1 to 6 carbon atoms.

Preferable examples of the aromatic ester solvent include benzyl esters such as benzyl acetate, etc.; phenyl esters such as phenyl acetate, etc.; tolyl esters such as p-tolyl acetate, etc.; 4-phenylbutyl esters such as 4-phenylbutyl acetate, etc.; benzoate esters such as methyl benzoate, ethyl benzoate, propyl benzoate, butyl benzoate, isoamyl benzoate, etc.; methyl benzoates such as ethyl 2-methyl bezoate, methyl 2-methylbenzoate, ethyl 3-methylbenzoate, ethyl 4-methylbenzoate, etc., phenyl propionates such as ethyl phenyl propionate, etc., phenyl acetates such as ethyl phenylacetate, etc.

The aromatic ester solvent is contained in the pesticidal emulsifiable concentrate of the present invention in an amount of 15 to 90% by weight, preferably 20 to 60% by weight.

The pesticidal emulsifiable concentrate of the present invention may further contain other solvents, additives, etc., in addition to the pesticidal active ingredient compound (a), the surfactant (b), and the aromatic ester solvent (c), if necessary.

Examples of the solvent include aromatic hydrocarbon solvents such as alkylbenzenes (ex. xylene, tetramethylbenzene, etc.), alkylnaphthalenes (ex. methylnaphthalene, etc.), diphenylethane, dixylylethane, phenylxylylethane, etc.; non-aromatic ester solvents such as methyl laurate, isopropyl myristate, isopropyl palmitate, methyl caprinate, methyl oleate, isobutyl oleate, butyl propionate, isoamyl propionate, ethyl butyrate, butyl butyrate, isoamyl butyrate, isoamyl isovalerate, amyl lactate, methyl linoleate, methyl linolenate, coconut fatty acid methyl, etc.; vegetable oils such as soybean oil, corn oil, rape seed oil, linseed oil, castor oil, cottonseed oil, peanut oil, sesame oil, etc.; aliphatic hydrocarbon solvents; alcohol solvents such as 2-ethyl hexanol, etc.; and ketone solvents such as cyclohexanone, acetophenone, etc.

Examples of the additives include antioxidants such as 3-/2-t-butyl-4-hydroxyanisole, butylatedhydroxytoluene, etc.; and pigments.

The pesticidal emulsifiable concentrate of the present invention are normally used as an agent for foliar treatment, or seed treatment.

When using in the foliar treatment, an emulsion prepared by diluting the pesticidal emulsifiable concentrate of the present invention with water (generally from about 100 to 5000 times) is normally applied to foliage, although the concentration varies depending on the kind and content of the active ingredient. Also, an emulsion prepared by diluting the pesticidal emulsifiable concentrate of the present invention with water (generally from about 10 to 5000 times) may be aerial-applied by a helicopter.

When using in the seed treatment, seeds are dipped in a dilution of the pesticidal emulsifiable concentrate of the present invention prepared by diluting with water (from about 10 to 100 times), or a dilution of the pesticidal emulsifiable concentrate of the present invention prepared by diluting with water (from about 2 to 100 times) is sprayed to seed.

The following Examples further illustrate the present invention in detail.

First, Formulation Examples of the pesticidal emulsifiable concentrate of the present invention will be shown. In the following Examples, "parts" are "parts by weight".

FORMULATION EXAMPLE 1

11 Parts of pyriproxyfen, 1.25 parts of Soprophor 796/P (surfactant manufactured by Rhone-Poulenc, polyoxyethylene polyoxypropylene polyaryl ether having HLB of 13.5), 3.75 parts of Geronol FF-4-E (surfactant manufactured by Rhone-Poulenc, containing 50% by weight of calcium dodecylbenzenesulfonate), 22 parts of benzyl acetate, and the residual parts of Solvesso 150 (manufactured by Exxon Co., aromatic hydrocarbon solvent having 9 to 11 carbon atoms) were combined to make 100 parts, followed by sufficient mixing to obtain a pesticidal emulsifiable concentrate of the present invention.

FORMULATION EXAMPLE 2

According to the same manner as that described in Formulation Example 1 except for using 44 parts of benzyl acetate in place of 22 parts of benzyl acetate, a pesticidal emulsifiable concentrate of the present invention was obtained.

FORMULATION EXAMPLE 3

11 Parts of pyriproxyfen, 10 parts of Sorpol 3816 (surfactant manufactured by Toho Chemical Industry Co., containing polyoxyethylene polyaryl ether, polyoxyethylene polyaryl ether polymer and calcium salt of alkylaryl sulfonate), 22 parts of benzyl acetate and the residual part of Solvesso 150 were combined to make 100 parts, followed by sufficient mixing to obtain a pesticidal emulsifiable concentrate of the present invention.

FORMULATION EXAMPLE 4

11 Parts of pyriproxyfen, 7 parts of Sorpol 3816, 44 parts of benzyl acetate and the residual part of Solvesso 150 were combined to make 100 parts, followed by sufficient mixing to obtain a pesticidal emulsifiable concentrate of the present invention.

FORMULATION EXAMPLE 5

11 Parts of pyriproxyfen, 10 parts of T-MULZ PB High (surfactant manufactured by Harcros Co., nonionic surfactant), 50 parts of benzyl acetate and the residual part of Solvesso 150 were combined to make 100 parts, followed by sufficient mixing to obtain a pesticidal emulsifiable concentrate of the present invention.

FORMULATION EXAMPLE 6

11 Parts of pyriproxyfen, 7 parts of Geronol FF-6-E (surfactant manufactured by Rhone-Poulenc Co., blend emulsifier containing polyoxyethylene polyaryl ether and calcium salt of alkylaryl sulfonate), 3 parts of Geronol FF-4-E, 50 parts of benzyl acetate and the residual part of Solvesso 150 were combined to make 100 parts, followed by sufficient mixing to obtain a pesticidal emulsifiable concentrate of the present invention.

FORMULATION EXAMPLE 7

11 Parts of pyriproxyfen, 7 parts of Geronol FF-6-E, 3 parts of Geronol FF-4-E and 79 parts of benzyl acetate were sufficiently mixed to obtain a pesticidal emulsifiable concentrate of the present invention.

FORMULATION EXAMPLE 8

5 Parts of Fenvalerate, 1.25 parts of Soprophor 796/P, 3.75 parts of Geronol FF-4-E, 25 parts of benzyl acetate and the residual part of Solvesso 150 were combined to make 100 parts, followed by sufficient mixing to obtain a pesticidal emulsifiable concentrate of the present invention.

FORMULATION EXAMPLE 9

According to the same manner as that described in Formulation Example 8 except for using 11 parts of Fenvalerate in place of 5 parts of Fenvalerate, a pesticidal emulsifiable concentrate of the present invention was obtained.

FORMULATION EXAMPLE 10

According to the same manner as that described in Formulation Example 8 except for using 5 parts of Permethrin in place of 5 parts of Fenvalerate, a pesticidal emulsifiable concentrate of the present invention was obtained.

FORMULATION EXAMPLE 11

According to the same manner as that described in Formulation Example 5 except for using 11 parts of Cypermethrin in place of 11 parts of pyriproxyfen, a pesticidal emulsifiable concentrate of the present invention was obtained.

FORMULATION EXAMPLE 12

According to the same manner as that described in Formulation Example 1 except for using 22 parts of p-tolyl acetate in place of 22 parts of benzyl acetate, a pesticidal emulsifiable concentrate of the present invention was obtained.

FORMULATION EXAMPLE 13

According to the same manner as that described in Formulation Example 1 except for using 22 parts of propyl benzoate in place of 22 parts of benzyl acetate, a pesticidal emulsifiable concentrate of the present invention was obtained.

Next, the stability on dilution of the pesticidal emulsifiable concentrate of the present invention with water will be illustrated by the Test Examples.

TEST EXAMPLE 1

Each of pesticidal emulsifiable concentrate (0.1 ml) of the present invention obtained in the Formulation Examples 1 to 7 was poured into a 100 ml tapped measuring cylinder filled with hard water (500 ppm). Then, each measuring cylinder was turned upside down in a rate of 30 times per minute, and the content liquid was mixed uniformly and allowed to stand. One hour after the beginning of standing, the presence or absence of the separation of the liquid was observed. As a result, no separation of the liquid was recognized in any pesticidal emulsifiable concentrate of the present invention. Two hours after the beginning of standing, no separation of the liquid was recognized.

Furthermore, the test for irritation to eyes of the pesticidal emulsifiable concentrate of the present invention will be shown.

TEST EXAMPLE 2

Eyes of rabbits were treated with the pesticidal emulsifiable concentrate (0.1 ml) of the present invention obtained in Formulation Example 5, and the eyelids were lightly closed for 1 second and, after 30 seconds, 300 ml of warm water was sprayed to rinse eyes for 1 minute. After 1 week, the degree and area of corneal opacity were examined. As a result, no corneal opacity was recognized.

The pesticidal emulsifiable concentrate of the present invention is an emulsifiable concentrate which is superior in emulsion stability on use after diluting with water, and has a property of low irritation.

What is claimed is:

1. A pesticidal emulsifiable concentrate, comprising (a) 1 to 60% by weight of pyriproxyfen, (b) 2 to 25% by weight of at least one surfactant and (c) 15 to 90% by weight of at least one aromatic ester solvent represented by formula:

or the formula:

wherein R represents a non-aromatic group having 1 to 6 carbon atoms; Ar represents an aromatic group; and X represents a single bond or an alkylene group having 1 to 6 carbon atoms.

2. The pesticidal emulsifiable concentrate according to claim 1 wherein the aromatic ester solvent (c) is selected from the group consisting of benzyl acetate, phenyl acetate, p-tolyl acetate, 4-phenylbutyl acetate, methyl benzoate, ethyl benzoate, propyl benzoate, butyl benzoate, isoamyl benzoate, ethyl 2-methylbenzoate, methyl 2-methylbenzoate, ethyl 3-methylbenzoate, ethyl 4-methylbenzoate, ethyl phenylpropionate, ethyl phenylacetate and mixtures thereof.

3. The pesticidal emulsifiable concentrate according to claim 2, wherein the surfactant (b) is nonionic surfactant and/or anionic surfactant.

4. The pesticidal emulsifiable concentrate according to claim 2, wherein the amounts of the pyriproxyfen, the surfactant (b) and the aromatic ester solvent (c) are 2 to 40% by weight, 2 to 10% by weight and 20 to 60% by weight, respectively.

5. The pesticidal emulsifiable concentrate according to claim 1, wherein the surfactant (b) is a nonionic surfactant, an anionic surfactant or a mixture thereof.

6. The pesticidal emulsifiable concentrate according to claim 5, wherein the amounts of the pyriproxyfen, the surfactant (b) and the aromatic ester solvent (c) are 2 to 40% by weight, 2 to 10% by weight and 20 to 60% by weight, respectively.

7. The pesticidal emulsifiable concentrate according to claim 1, wherein the pyriproxyfen is present in an amount of 2 to 40% by weight, the surfactant (b) is present in an amount of 2 to 10% by weight, and the aromatic ester solvent (c) is present in an amount of 20 to 60% by weight.

8. The pesticidal emulsifiable concentrate according to claim 1, wherein the aromatic ester solvent (c) is represented by formula (2).

9. The pesticidal emulsifiable concentrate according to claim 1, wherein the aromatic ester solvent (c) is selected from the group consisting of benzyl acetate, phenyl acetate, p-tolyl acetate, and 4-phenylbutyl acetate.

10. The pesticidal emulsifiable concentrate according to claim 1, wherein the aromatic ester solvent (c) is selected from the group consisting of phenyl acetate, p-tolyl acetate, 4-phenylbutyl acetate, ethyl benzoate, propyl benzoate, butyl benzoate, isoamyl benzoate, ethyl 2-methylbenzoate, methyl 2-methylbenzoate, ethyl 3-methylbenzoate, ethyl 4-methylbenzoate, ethyl phenylpropionate and ethyl phenylacetate.

11. The pesticidal emulsifiable concentrate according to claim 1, wherein the aromatic ester solvent (c) is methyl benzoate.

12. The pesticidal emulsifiable concentrate according to the claim 1, wherein the aromatic ester solvent (c) is benzyl acetate.

13. The pesticidal emulsifiable concentrate according to claim 1, wherein the aromatic ester solvent (c) is selected from the group of phenyl acetate, p-tolyl acetate and 4-phenylbutyl acetate.

* * * * *